United States Patent [19]

Miyazaki et al.

[11] Patent Number: 4,585,890

[45] Date of Patent: Apr. 29, 1986

[54] PROCESS FOR PRODUCING ETHYLENE GLYCOL AND/OR GLYCOLIC ACID ESTER, CATALYST COMPOSITION USED THEREFOR, AND PROCESS FOR PRODUCTION THEREOF

[75] Inventors: Haruhiko Miyazaki; Taizo Uda; Koichi Hirai; Yasuo Nakamura, all of Ube; Harumi Ikezawa, Onoda; Takanori Tsuchie, Ube, all of Japan

[73] Assignee: UBE Industries, Ltd., Yamaguchi, Japan

[21] Appl. No.: 586,753

[22] Filed: Mar. 6, 1984

Related U.S. Application Data

[62] Division of Ser. No. 370,555, Apr. 21, 1982, Pat. No. 4,440,873.

[30] Foreign Application Priority Data

Apr. 30, 1981 [JP] Japan .................................. 56-64015

[51] Int. Cl.[4] ..................... C07C 67/333; C07C 31/20
[52] U.S. Cl. .................................... 560/179; 568/864
[58] Field of Search ....................... 560/179; 568/864; 252/454

[56] References Cited

U.S. PATENT DOCUMENTS

| | | | |
|---|---|---|---|
| 2,305,104 | 12/1942 | Pardee | 568/864 |
| 2,386,518 | 10/1945 | Upham | 502/320 |
| 2,891,094 | 6/1959 | Karkalits, Jr. et al. | 564/420 |
| 3,637,528 | 1/1972 | Stiles | 502/236 |
| 3,862,055 | 1/1975 | Eurlings et al. | 502/324 |
| 3,886,219 | 5/1975 | Fujita et al. | 568/881 |
| 3,886,319 | 5/1975 | Reich | 179/18 FA |
| 4,174,300 | 11/1979 | Koritala | 502/234 |
| 4,184,982 | 1/1980 | Schroeder et al. | 502/234 |
| 4,199,479 | 4/1980 | Wilkes | 568/864 |
| 4,511,744 | 4/1985 | Miyazaki et al. | 568/864 |

FOREIGN PATENT DOCUMENTS

575380 2/1946 United Kingdom .

OTHER PUBLICATIONS

*Encyclopaedia Chimica*, vol. 6, pp. 310-311.

*Primary Examiner*—Natalie Trousof
*Assistant Examiner*—Bruce D. Gray
*Attorney, Agent, or Firm*—Sherman & Shalloway

[57] ABSTRACT

A hydrogenation catalyst composition useful for the hydrogenation of an oxalate diester, said composition being composed of a reduction product of copper-containing silica gel formed by contacting an ammine complex of copper with colloidal silica sol; and a process for producing the aforesaid composition. Using a catalyst composed of the aforesaid composition, ethylene glycol and/or a glycolic acid ester can be produced from an oxalate diester efficiently with high conversions and selectivities and without causing pollution attributed to the use of a chromium-containing catalyst composition.

7 Claims, No Drawings

PROCESS FOR PRODUCING ETHYLENE GLYCOL AND/OR GLYCOLIC ACID ESTER, CATALYST COMPOSITION USED THEREFOR, AND PROCESS FOR PRODUCTION THEREOF

This is a division of application Ser. No. 370,555, filed Apr. 21, 1982, now U.S. Pat. No. 4,440,873 issued Apr. 3, 1984.

This invention relates to a commercial process for producing ethylene glycol and/or a glycolic acid ester from an oxalate diester efficiently with high conversions and selectivities and without causing pollution attributed to the use of a chromium-containing catalyst composition. The invention also relates to a catalyst composition for use in the aforesaid process, and to a process for producing the catalyst composition.

More specifically, this invention relates to a hydrogenation catalyst composition useful for the hydrogenation of an oxalate diester, composed of a reduction product of copper-containing silica gel formed by contacting an ammine complex of copper with colloidal silica sol. This catalyst composition is prepared by contacting an ammine complex of copper with colloidal silica sol in the presence of an aqueous medium to form copper-containing silica gel, and subjecting the copper-containing silica gel to reduction. The invention also pertains to a process for producing ethylene glycol and/or a glycolic acid ester, which comprises hydrogenating an oxalate diester in the gaseous or vapor phase at an elevated temperature in the presence of the aforesaid catalyst composition.

It is known to prepare ethylene glycol and/or a glycolic acid ester by the catalytic hydrogenation of an oxalate diester in the gaseous or vapor phase at an elevated temperature in the presence of a hydrogenation catalyst, and a Cu/Cr type catalyst has already been proposed as the hydrogenation catalyst (see Japanese Patent Publication No. 42971/1980 corresponding to U.S. Pat. No. 4,112,245; and German Pat. No. 459,603). On the other hand, Japanese Laid-Open Patent Publication No. 40685/1980 discloses a catalyst comprising ruthenium, nickel and Raney nickel.

Cu/Cr type catalysts are generally known as catalysts which can be utilized to hydrogenate esters to the corresponding alcohols. In practice, however, the use of this type of Cr-containing catalysts causes troubles. It is extremely difficult, if not impossible by a complicated and expensive operation, to recover chromium efficiently and completely from a spent Cu/Cr type catalyst, and such a catalyst is not suitable for industrial operations. Since chromium, even in trace, exhibits strong toxicity to humans, discarding of chromium-containing catalyst residues in general environments should be avoided. This leads to the defect that the high catalytic activity of the Cu/Cr type catalysts is reduced in practice because of the difficulty of disposing of the spent catalysts.

It is generally known that various other metals or metal compounds can be used as hydrogenation catalysts or their components. Examples include Raney nickel, nickel, cobalt, copper, iron, platinum, and palladium, and their oxides and sulfides. It is well known that these generally known metals or metal compounds are not necessarily useful in any catalytic hydrogenation reactions, and a desired hydrogenation reaction cannot be carried out efficiency unless a catalyst suitable for the desired hydrogenation is selected according to the mode of the reaction, the hydrogenation reaction conditions, etc. It is also widely known that no established guideline exists for selecting such a suitable catalyst.

We have extensively worked in order to develop a catalyst composition for the catalytic hydrogenation of an oxalate diester, which is free from chromium and has a better catalytic activity than that of conventional catalysts for the catalytic hydrogenation of an oxalate diester.

Consequently, we have found that a catalyst composition composed of a reduction product of copper-containing silica gel formed by contacting an ammine complex of copper with colloidal silica sol is useful for forming ethylene glycol and/or a glycolic acid ester efficiently from an oxalate diester in higher conversions and selectivities with industrial advantage than the known Cu-Cr catalysts and can overcome the trouble of conventional chromium-containing catalyst compositions. It has also been found that this catalyst composition can be prepared by contacting an ammine complex of copper with colloidal silica sol to form copper-containing silica gel, and subjecting the resultant copper-containing silica gel to reduction, and that this catalyst looks black to the naked eye. In contrast, a conventional copper-containing catalyst supported on silica gel prepared by depositing a copper compound on a silica gel carrier and then subjecting it to reduction looks brown to the naked eye.

It is an object of this invention therefore to provide a hydrogenation catalyst composition for the hydrogenation of an oxalate diester.

A second object of this invention is to provide a process for producing the aforesaid hydrogenation catalyst.

A third object of this invention is to provide a process for producing ethylene glycol and/or a glycolic acid ester from an oxalate diester in the presence of the aforesaid hydrogenation catalyst.

The above and other objects and advantages of this invention will become more apparent from the following description.

The hydrogenation catalyst composition of this invention can be produced by a process which comprises contacting an ammine complex of copper with colloidal silica sol, and subjecting the resulting copper-containing silica gel to reduction. According to its one embodiment, an aqueous solution containing an ammine complex of copper is mixed with colloidal silica sol. At this stage, the silica sol changes to silica gel and a copper ion is simultaneously supported on the gel. The resultant copper-containing silica gel is subjected to a reducing treatment in the presence of hydrogen gas.

The aqueous solution containing an ammine complex of copper can be prepared by a method known per se. For example, it can be prepared by adding ammonia to an aqueous solution containing a copper ion until the solution becomes alkaline. It can also be prepared by adding copper flakes to a concentrated aqueous solution of ammonia and passing air through the mixture.

The aqueous solution containing a copper ion can be obtained by dissolving a water-soluble copper compound (including copper salts) in water. Examples of such copper compounds are copper nitrate, copper sulfate, copper oxalate, copper chloride, and copper acetate. Cupric nitrate is especially preferred.

The colloidal silica sol is commercially available, and commercial colloidal silica sols can be used in this invention. It can also be prepared by known methods. An example of such methods is described, for example, at pages 331 to 334 of "The Chemistry of Silica", John Wiley & Sons, Inc., New York, 1979.

According to one example of the aforesaid embodiment, the catalyst composition of this invention can be produced by the following procedure.

Such a water-soluble copper compound as exemplified above, for example cupric nitrate, is dissolved in water, and conc. aqueous ammonia is added to the resulting aqueous solution containing a cupric ion until the pH of the mixture reaches at least about 10, for example about 10 to about 12. Thus, a deep blue aqueous solution forms. Colloidal silica sol is added to the deep blue aqueous solution, and they are stirred to mix and contact them fully with each other. The mixing can be effected either at room temperature or at elevated temperatures, for example at room temperature to about 150° C., under atmospheric or elevated pressures. Elevated temperatures, for example about 40° to about 100° C., are preferred. As a result, the silica sol is converted to silica gel and at this stage, a copper ion is supported on the silica gel to form copper-containing silica gel. The resulting product is subjected, for example, to an evaporating treatment to form a solid residue which is then washed fully with water and dried. The dried residue is then subjected to a reducing treatment to obtain the catalyst composition of this invention. Instead of the evaporation treatment, a concentrating treatment may be used. For example, the product may be concentrated to about one-half of its original amount, and a solid is recovered from it by, for example, filtration and then treated similarly to the above to obtain the catalyst composition of this invention.

The evaporating treatment and the concentrating treatment may be carried out under atmospheric, reduced or elevated pressures. These treatments can be effected at room temperature or at elevated temperatures. The use of elevated temperatures, for example about 60° to about 90° C., is preferred.

The reducing treatment can be carried out in accordance with a known method by treating the resulting copper-containing silica gel with hydrogen at an elevated temperature. For example, the reducing treatment can be carried out by heat-treating the copper-containing silica gel with hydrogen at about 150° to about 500° C., preferably at about 200° to about 400° C., for about 1 to about 15 hours. Prior to the reducing treatment, the copper-containing silica gel may be preliminarily heat-treated. For example, the preliminary heat-treatment can be carried out by calcining it in the air at a temperature of about 400° to about 800° C., preferably about 500° to about 750° C., for about 1 to about 10 hours.

The hydrogenation catalyst composition obtained as above and composed of a reduction product of copper-containing silica gel formed by contacting an ammine complex of copper with colloidal silica sol looks black to the naked eye.

The copper content of the catalyst composition of this invention, in terms of the weight ratio of $SiO_2:Cu$, can be adjusted by properly selecting the amounts of the ammine complex of copper and colloidal silica sol during the preparation of the catalyst composition. Preferably, the weight ratio of $SiO_2:Cu$ is from 1:about 0.001 to 1:about 2, more preferably from 1:about 0.01 to 1:about 1.

According to this invention, there is provided, in a process for producing ethylene glycol and/or a glycolic acid ester which comprises hydrogenating an oxalate diester in the gaseous or vapor phase at an elevated temperature in the presence of a hydrogenation catalyst, the improvement wherein the hydrogenation catalyst is the catalyst composition of the present invention composed of a reduction product of copper-containing silica gel formed by contacting an ammine complex of copper with colloidal silica sol. This process is carried out in a customary manner except that the specific catalyst composition of this invention is used. For example, it can be carried out by using the processes disclosed in Japanese Patent Publication No. 42971/1980 (corresponding to U.S. Pat. No. 4,112,245), German Pat. No. 459,603, and Japanese Laid-Open Patent Publication No. 40685/1980.

The starting oxalate diester used in the process of this invention is preferably a di($C_1$–$C_8$)alkyl ester of oxalic acid. Examples include dimethyl oxalate, diethyl oxalate, dibutyl oxalate and diamyl oxalate.

The reaction conditions in the presence of the catalyst composition of this invention can be properly selected in accordance with known methods. For example, preferred reaction conditions are as follows:

Reaction temperature

About 140° to about 300° C., preferably about 170° to about 260° C., more preferably about 180° to about 240° C.

Contact time (based on STP)

About 0.01 to about 20 seconds (about 0.02 to about 40 g·sec/ml), preferably about 0.2 to about 5 seconds (about 0.4 to about 10 g·sec/ml).

Reaction pressure

About 0.1 to about 200 atmospheres, preferably about 1 to about 40 atmospheres.

Mole ratio of hydrogen to oxalate diester

At least about 4, preferably about 10 to about 500.

The catalytic hydrogenation reaction of the oxalate diester can be carried out in any mode by contacting the oxalate diester with hydrogen gas and the catalyst composition in the gaseous or vapor phase in a fixed catalyst bed or a fluidized catalyst bed. The reaction can be performed either batchwise or continuously.

The hydrogenating catalyst of the invention does not contain chromium, as is apparent from the method of its preparation. Despite the fact that it does not contain chromium, the catalyst of the invention can efficiently catalyze a reaction of hydrogenating an oxalate diester to ethylene glycol and/or a glycolic acid ester, and the desired product can be obtained in a higher space time yield than in the case of using the known catalysts. Accordingly, the hydrogenating catalyst of this invention is particularly suitable for the industrial production of ethylene glycol and/or a glycolic acid ester from an oxalate diester.

By hydrogenating the oxalate diester in the presence of the hydrogenating catalyst composition of this invention, both ethylene glycol and a glycolic acid ester are generally formed. Ethylene glycol, or the glycolic acid ester, or both can be separated and recovered from the reaction products by any desired methods.

The following examples illustrate the present invention more specifically.

EXAMPLE 1

19.0 g of cupric nitrate trihydrate [$Cu(NO_3)_2.3H_2O$] was dissolved in 200 ml of water, and 60 ml of a conc. aqueous solution of ammonia was added to adjust the pH of the solution to about 11 to 12 and give a deep blue solution containing a copper ammine complex. To the deep blue solution was added 66.6 g of 30% by weight colloidal silica sol, and they were stirred at room temperature for several hours. The temperature of the solution was then raised to evaporate most of the water, and the residue was dried at 120° C. for 12 hours. The dried product was fully washed with water, and again dried in the air at 140° C. for 14 hours. The dried product was reduced in a stream of hydrogen at 350° C. for 2 to 3 hours to prepare a catalyst having a copper content of about 20% by weight. The weight ratio of $SiO_2$ to Cu was 1:about 0.25.

0.5 g of the catalyst prepared as above was filled in a stainless steel reaction tube having an inside diameter of 4 mm, and diethyl oxalate was catalytically hydrogenated in it at a reaction temperature of 215° C. and a reaction pressure of 0.5 kg/cm$^2$·G while maintaining the contact time at 0.75 g·sec/ml (based on STP). The mole ratio of hydrogen to diethyl oxalate fed to the reaction system was maintained at 70.

Analysis of the reaction product showed that the conversion of diethyl oxalate was 99.8%, the selectivity for ethylene glycol was 87.5%, and the selectivity for ethyl glycolate was 11.4%.

EXAMPLES 2 TO 4

Diethyl oxalate was catalytically hydrogenated in the same way as in Example 1 except that the reaction temperature and the mole ratio of hydrogen to diethyl oxalate were changed as shown in Table 1. The results are shown in Table 1.

TABLE 1

| Example | Reaction temperature (°C.) | Mole ratio of hydrogen to diethyl oxalate | Conversion of diethyl oxalate (%) | Selectivity for ethylene glycol (%) | Selectivity for ethyl glycolate (%) |
| --- | --- | --- | --- | --- | --- |
| 2 | 188 | 300 | 100 | 99.5 | 0 |
| 3 | 209 | 70 | 99.5 | 80.8 | 15.4 |
| 4 | 215 | 50 | 98.4 | 87.2 | 10.1 |

EXAMPLE 5

3.8 g of cupric nitrate trihydrate was dissolved in 50 ml of water, and 12 ml of a conc. aqueous solution of ammonia was added to adjust the pH of the solution to about 11 to 12 and give a deep blue solution containing a copper ammine complex. To the deep blue solution was added a solution of 66.6 g of 30% by weight colloidal silica sol in 50 ml of distilled water, and the mixture was stirred at room temperature for several hours. The mixture was heated to evaporate most of the water, and further dried at 120° C. for 12 hours. Then, the dried product was fully washed with water, and again dried at 140° C. for 14 hours. The dried product was reduced in a stream of hydrogen at 350° C. for 2 hours to prepare a catalyst containing about 5% by weight of copper. The weight ratio of $SiO_2$ to Cu was 1:about 0.05.

0.5 g of the resulting catalyst was filled in a stainless steel reaction tube having an inside diameter of 4 mm, and diethyl oxalate was hydrogenated in it at a reaction temperature of 225° C. and a reaction pressure of 0.5 kg/cm$^2$·G while maintaining the contact time at 0.75 g·sec/ml (based on STP). The mole ratio of hydrogen to diethyl oxalate fed to the reaction system was maintained at 200.

Analysis of the reaction product showed that the conversion of diethyl oxalate was 99.1%, the selectivity for ethylene glycol was 87.1%, and the selectivity for ethyl glycolate was 7.1%.

EXAMPLES 6 AND 7

Diethyl oxalate was hydrogenated in the same way as in Example 5 except that the reaction temperature and the mole ratio of hydrogen to diethyl oxalate were changed as shown in Table 2.

TABLE 2

| Example | Reaction temperature (°C.) | Mole ratio of hydrogen to diethyl oxalate | Conversion of diethyl oxalate (%) | Selectivity for ethylene glycol (%) | Selectivity for ethyl glycolate (%) |
| --- | --- | --- | --- | --- | --- |
| 6 | 215 | 200 | 94.7 | 60.3 | 35.1 |
| 7 | 235 | 150 | 100 | 84.6 | 3.4 |

EXAMPLES 8 TO 11

506 g of cupric nitrate trihydrate was dissolved in 1500 ml of water, and 1500 ml of a conc. aqueous solution of ammonia was added to adjust the pH of the solution to about 11 to 12 and give a deep blue solution of copper ammine complex. The deep blue solution was mixed with a solution of 666 g of 30% by weight colloidal silica sol in 500 ml of water, and the mixture was stirred at room temperature for several hours. The temperature of the mixture was raised to evaporate most of the water, and the residue was dried at 120° C. for 16 hours. The dried product was fully washed with water, and again dried at 120° C. for 24 hours. The dried product was reduced in a stream of hydrogen at 300° C. for 2.5 hours to prepare a catalyst containing about 40% by weight of copper. The weight ratio of $SiO_2$ to Cu was 1:about 0.67.

0.5 g of the resulting catalyst was filled in a stainless steel reaction tube having an inside diameter of 4 mm, and diethyl oxalate was hydrogenated in it under a reaction pressure of 0.5 kg/cm$^2$·G while maintaining the contact time at 0.75 g·sec/ml (based on STP). The reaction temperature was varied as shown in Table 3. The results are shown in Table 3.

TABLE 3

| Example | Reaction temperature (°C.) | Mole ratio of hydrogen to diethyl oxalate | Conversion of hydrogen oxalate (%) | Selectivity for ethylene glycol (%) | Selectivity for ethyl glycolate (%) |
| --- | --- | --- | --- | --- | --- |
| 8 | 190 | 92 | 90.0 | 47.8 | 45.2 |
| 9 | 205 | 92 | 100 | 87.5 | 2.5 |
| 10 | 215 | 11 | 43.6 | 45.4 | 44.6 |
| 11 | 225 | 11 | 69.7 | 46.8 | 43.7 |

EXAMPLES 12 TO 16

The same dried product as obtained in Example 1 was calcined at 500° C. for 5 hours in the air and then subjected to a reducing treatment in hydrogen at 350° C. for 2 hours to form a catalyst in which the mole ratio of $SiO_2$ to Cu was 1:about 0.25.

0.56 g of the resulting catalyst was filled in a stainless steel reaction tube having an inside diameter of 4 mm, and diethyl oxalate was hydrogenated under the conditions shown in Table 4 with a contact time of 0.8 g·sec/ml (based on STP). The results are shown in Table 4.

TABLE 4

| Example | Reaction temperature (°C.) | Reaction pressure (kg/cm² · G) | Mole ratio of hydrogen to diethyl oxalate | Conversion of diethyl oxalate (%) | Selectivity for ethylene glycol (%) | Selectivity for ethyl glycolate (%) |
| --- | --- | --- | --- | --- | --- | --- |
| 12 | 200 | 0.5 | 50 | 58.4 | 12.6 | 79.3 |
| 13 | 215 | 0.5 | 50 | 98.8 | 53.0 | 38.7 |
| 14 | 235 | 0.5 | 11 | 74.1 | 25.4 | 51.7 |
| 15 | 215 | 3 | 30 | 100 | 97.2 | 2.6 |
| 16 | 235 | 3 | 30 | 100 | 72.6 | 0.4 |

COMPARATIVE EXAMPLE 1

15.5 g of cupric nitrate trihydrate was dissolved in 400 ml of water, and 170 g of 20% by weight colloidal silica sol was added little by little with stirring at room temperature. Then, an aqueous solution of sodium hydroxide obtained by dissolving 5.2 g of sodium hydroxide in 100 ml of water was added little by little to form a precipitate. The precipitate was collected by filtration, washed fully with water, and dried in the air at 120° C. for 15 hours, and subjected to a reducing treatment in a stream of hydrogen at 350° C. for 2 hours. The weight ratio of $SiO_2$ to Cu in the resulting catalyst was 1:about 0.12.

0.5 g of the resulting catalyst was filled in a stainless steel reaction tube having an inside diameter of 4 mm, and diethyl oxalate was hydrogenated in it at 230° C., atmospheric pressure and a space velocity of 3700 hr$^{-1}$ while maintaining the contact time at 1.5 g·sec/ml (based on STP). The mole ratio of hydrogen to diethyl oxalate fed to the reaction system was adjusted to 200.

Analysis of the reaction product showed that the conversion of diethyl oxalate was 53.5%, the selectivity for ethyl glycolate was 73.0%, and the selectivity for ethylene glycol was about 0%.

EXAMPLE 17

The dried product obtained in Example 8 (the product before the reducing treatment) was molded into pellets having a size of 5 mm×5 mm. The pellets were pulverized to a size of 9 to 16 mesh and reduced in a stream of hydrogen at 200° C. for 5 hours to form a catalyst in which the weight ratio of $SiO_2$ to Cu was 1:about 0.67.

25 ml of the resulting catalyst was filled in a stainless steel reaction tube having an inside diameter of 19.4 mm, and dimethyl oxalate was hydrogenated at a reaction temperature of 201° C., a total pressure of 20 kg/cm²·G and a liquid hourly space velocity of 0.66 g/ml.hr, and a space velocity of 6150 hr$^{-1}$ while maintaining the mole ratio of hydrogen to dimethyl oxalate at 40.6.

Analysis of the reaction product showed that the conversion of dimethyl oxalate was 100%, the selectivity for ethylene glycol was 97.2%, and the selectivity for methyl glycolate was 0.7%.

COMPARATIVE EXAMPLE 2

A copper-chromite catalyst (a product of Nikki Chemical Co., Ltd.; CuO 36%, $Cr_2O_3$ 45%, $MnO_2$ 9%, by weight) was pulverzed to a size of 9 to 16 mesh, and reduced in a stream of hydrogen while raising the temperature slowly from room temperature to 150° C. It was maintained at 150° to 160° C. for several hours. Then, the temperature was again slowly raised to 200° C., and the product was maintained at 200° C. for several hours to perform reduction. 25 ml of the catalyst so reduced was filled in a stainless steel reaction tube having an inside diameter of 19.4 mm, and dimethyl oxalate was hydrogenated at a reaction temperature of 203° C., a liquid hourly space velocity of 0.62 g/ml·hr., a space velocity of 6530 hr$^{-1}$, and a total pressure of 20 kg/cm²·G while maintaining the mole ratio of hydrogen to dimethyl oxalate at 43.4.

Analysis of the reaction product showed that the conversion of dimethyl oxalate was 93.2%, the selectivity for ethylene glycol was 86.2%, and the selectivity for methyl glycolate was 7.6%.

EXAMPLE 18

30.31 g of cupric nitrate trihydrate was dissolved in 120 ml of distilled water, and 90 ml of 28% aqueous ammonia was added to prepare a copper-ammine complex solution. The solution was mixed with 39.96 g of 30% by weight colloidal silica sol, and the mixture was stirred at room temperature for 20 to 30 minutes. The mixed solution was heated to 80° to 90° C. to evaporate water so that the total volume of the solution was reduced to about one-half. The residue was filtered, fully washed, and dried at 120° C. overnight, and subjected to a reducing treatment in a stream of hydrogen at 200°

C. to give a catalyst containing 39.5% of copper. The weight ratio of $SiO_2$ to Cu in the catalyst was 1:about 0.67.

0.5 g of the resulting catalyst was filled in a stainless steel reaction tube having an inside diameter of 4 mm, and diethyl oxalate was hydrogenated in it at a pressure of 0.5 kg/cm$^2$·G and a temperature of 210° C. while maintaining the contact time at 0.75 g·sec/ml (based on STP) and the mole ratio of hydrogen to diethyl oxalate at about 70.

Analysis of the reaction product showed that the conversion of diethyl oxalate was 100%, the selectivity for ethylene glycol was 93.0%, and the selectivity for ethyl glycolate was 3.6%.

EXAMPLE 19

25.3 g of cupric nitrate trihydrate was dissolved in 75 ml of distilled water. Then, 75 ml of 28% by weight aqueous ammonia was added to the solution to prepare a copper-ammine complex solution. The solution was stirred for about 15 minutes, and then mixed with 33.3 g of 30% by weight colloidal silica sol. The mixture was stirred for about 15 minutes, and transferred to a 500 ml flask in a rotary evaporator connected to an aspirator.

The mixture was subjected to evaporation at 80° to 90° C. under reduced pressure for about 2 hours. Upon completion of the evaporation, the solid residue obtained was blue and not brown. The solid residue was transferred to an oven and dried overnight at 120° C. The color of the solid residue remained blue. It was then subjected to a reducing treatment in a stream of hydrogen at about 200° C. for 5 hours to obtain a catalyst in which the weight ratio of $SiO_2$ to Cu was 1:about 0.6.

What we claim is:

1. In a process for producing ethylene glycol and/or a glycolic acid ester which comprises hydrogenating an oxalate diester in the vapor phase at an elevated temperature in the presence of a hydrogenation catalyst, the improvement wherein the catalyst is a catalyst composition composed of a reduction product of copper-containing silica gel formed by contacting an ammine complex of copper with colloidal silica sol.

2. The process of claim 1 wherein the oxalate diester is at least one di($C_1$–$C_8$)alkyl ester of oxalic acid.

3. The process of claim 1 wherein the elevated temperature is about 140° to about 300° C.

4. The process of claim 1 wherein the mole ratio of hydrogen to the oxalate diester is about 4 or more.

5. The process of claim 1 wherein the weight ratio of $SiO_2$ to Cu is from 1:about 0.001 to 1:about 2.

6. The process of claim 1 wherein the weight ratio of $SiO_2$ to Cu is from about 1:about 0.01 to 1:about 1.

7. The process of claim 6 wherein the oxalate diester is at least one di($C_1$–$C_8$)alkyl ester of oxalic acid and wherein the hydrogenation reaction is carried out at an elevated temperature of from about 140° to 300° C. and a pressure of from about 0.1 to 200 atmospheres, and wherein the mole ratio of hydrogen to the oxalate diester is about 4 or more.

* * * * *